United States Patent [19]
Monroe et al.

[11] Patent Number: 5,907,870
[45] Date of Patent: Jun. 1, 1999

[54] ANATOMICALLY-ACCURATE SURGICAL GLOVE

[75] Inventors: Lance Allan Monroe, Plymouth, Minn.; Steven Jeffrey Sherrill, Richmond, Va.; Laura Elizabeth Poindexter, San Diego, Calif.

[73] Assignee: Safeskin Corporation, Boca Raton, Fla.

[21] Appl. No.: 08/943,273

[22] Filed: Oct. 3, 1997

Related U.S. Application Data

[60] Provisional application No. 60/027,626, Oct. 4, 1996.

[51] Int. Cl.⁶ .................................................. A41D 19/00

[52] U.S. Cl. ...................................... 2/161.7; 2/168; 2/163

[58] Field of Search ........................... 2/161.7, 168, 163, 2/159, 161.6, 167

[56] References Cited

U.S. PATENT DOCUMENTS

| | | | |
|---|---|---|---|
| 1,241,941 | 10/1917 | Dowd | 2/168 |
| 1,279,855 | 9/1918 | Garvey | 2/168 |
| 2,036,413 | 4/1936 | Herbruck | 2/168 |
| 2,075,550 | 3/1937 | Smith | 2/168 |
| 2,335,871 | 12/1943 | Milligan | 2/168 |
| 4,218,778 | 8/1980 | Stansbury | 2/168 |
| 5,442,816 | 8/1995 | Seketa | 2/168 |
| 5,687,424 | 11/1997 | Masley | 2/168 |

*Primary Examiner*—Amy B. Vanatta
*Attorney, Agent, or Firm*—Rothwell Figg Ernst & Kurz

[57] ABSTRACT

A surgical glove, manufactured from an elastomeric material, includes an enlarged thumb ball portion which extends across the entire width of the palm, from the base of the thumb to the base of the fifth finger. The enlarged thumb ball portion improves the comfort of the glove. The glove also features independently-curved fingers and a cuff portion.

8 Claims, 2 Drawing Sheets

5,907,870

ANATOMICALLY-ACCURATE SURGICAL GLOVE

This application is a provision Ser. No. 60/027,626 filed Oct. 4, 1996.

BACKGROUND OF THE INVENTION

The present invention relates to latex surgical gloves. More particularly, the present invention relates to an improved latex surgical glove, the configuration of which provides increased comfort and sensitivity to the wearer.

The fit-and sensitivity of a surgeon's latex glove are extremely important. Surgeons perform many delicate procedures, often using very small tools, and thus require a high degree of tactile sensitivity. Additionally, surgical procedures can require the surgeon (and others) to wear surgical gloves over a span of many-hours. Maintaining the desired sensitivity over that time span, as well as comfort, are important attributes of surgical gloves.

"Surgical gloves" are used in contexts other than during surgery as well as in industries outside of the medical field. For example, individuals assembling electronic equipment may wear close-fitting latex gloves which, for the purposes of this patent, can also be classified as "surgical gloves." The issues regarding tactile sensitivity and long-term comfort faced by these persons are the same or similar to those faced by surgeons and others in the medical field.

Accordingly, it would be desirable to provide an improved latex surgical glove which provides good tactile sensitivity and improved comfort during long-term wear by persons working in medical and other professions and industries.

SUMMARY OF THE INVENTION

The foregoing has been attained by the present invention which provides an improved, anatomically-accurate surgical glove. The glove according to the present invention includes an enlarged thumb ball portion which extends fully across the width of the hand from the base of the thumb to a side of the hand opposite the thumb. The glove advantageously also has the fingers arranged independently curved, in an array in which the fingers wrap around the back of the hand along an arc. The bottom portion of the glove may include a cuff portion of reduced diameter.

BRIEF DESCRIPTION OF THE DRAWINGS

The invention may be better understood by reference to the accompanying drawings, in which.

DETAILED DESCRIPTION OF THE PREFERRED EMBODIMENTS

Figure 1:
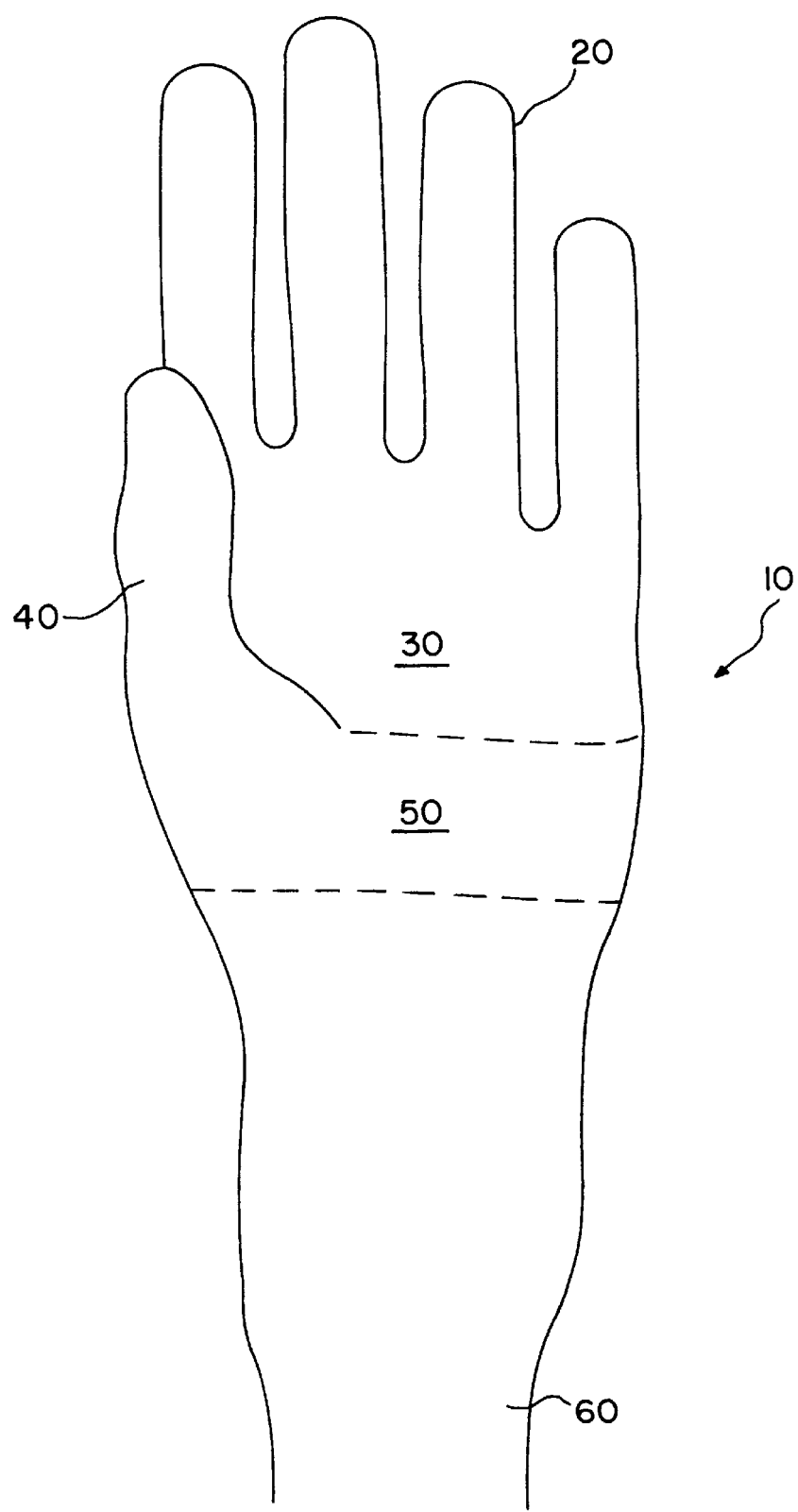
FIG. 1 is a front view of a surgical glove according to the present invention.

Referring now to the Figures, a surgical glove according to the present invention is depicted by FIG. 1 and referred to generally by reference numeral 10. The glove includes a plurality of finger portions 20, a palm region 30, a thumb portion 40 and a thumb ball area 50.

Figure 3:
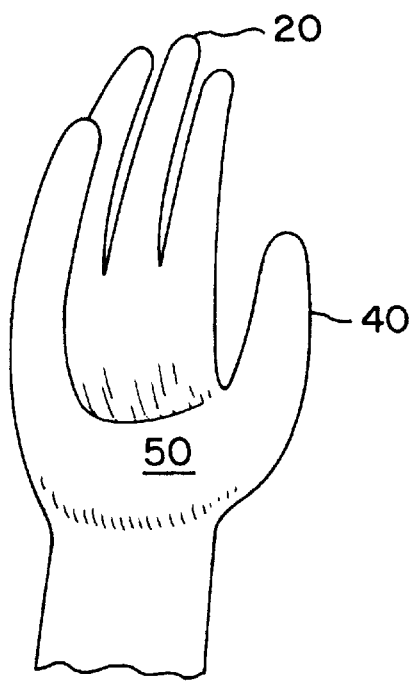
FIG. 3 is a perspective view of the glove of FIG. 2.

As seen in FIG. 1, the thumb ball area 50 extends across the entire width of the palm region 30 of the glove. Thumb ball area 50 extends from the base of the thumb portion 40, across the entire width of the palm region 30, to the edge of the glove below the fifth finger. As seen best in FIG. 3, the thumb ball area 50 merges with and is integral with the portion of the palm region 30 immediately below the fifth finger.

The enlarged thumb ball area 50 of the glove provides increased comfort to the wearer. The enlarged thumb ball area 50 serves to increase the circumference of the glove throughout the lower palm area, which reduces the amount that the glove must stretch when the wearer's hand moves into certain positions. Reducing the need for the latex to stretch in turn lowers the pressure that the latex exerts on the wearer's hand, thus providing increased comfort. Further, the geometry of the glove better resembles the anatomy of the human hand which includes a muscular, "fleshy" region below the fifth finger.

Figure 2:
FIG. 2 is a perspective view of a glove according to the present invention.

The finger portions 20 of the glove, as seen in FIG. 2, are independently curved and wrap around the hand along a common arc. This arrangement adds to the comfort of the glove, inasmuch as the arrangement better resembles the anatomy of the human hand when the hand is relaxed.

Optionally, the glove 10 includes a reduced-diameter cuff portion 60. This cuff portion helps, for example, to grip the wearer's wrist or forearm and to prevent the glove from sliding down the surgeon's gown, or another article of clothing of the wearer, during use.

The glove according to the present invention may be manufactured from any of the elastomeric materials commonly employed in the manufacture of surgical and other gloves. The glove can be manufactured from, for example, natural latex, natural latex that has been treated, for example, to reduce antigenicity, silicone rubber or nitrile rubber. Further, the glove may be manufactured for end uses other than as a surgeon's glove. Workers in various medical and high technology manufacturing industries commonly use close-fitting elastomeric gloves; the glove of the present invention will be useful in all of these contexts.

Although the present invention has been described in connection with certain preferred versions and configurations, it is not so limited. Modifications to the illustrated configurations, within the scope of the claims, will be apparent to those skilled in the art.

What is claimed is:

1. An anatomically-accurate elastomeric surgical glove, comprising:

a palm region;

a plurality of finger portions which extend from base ends of said finger portions upward from said palm region;

a thumb portion at one side of a width of said glove; and an enlarged thumb ball area which extends across said width of said glove below said palm region from a base of the thumb portion to a side of the glove opposite the thumb portion at an edge of the glove below a fifth finger portion and which increases the circumference of the glove across a lower portion of said glove below said palm region to reduce the amount that the glove stretches when a wearer's hand moves into certain positions;

wherein said thumb ball region is substantially below said base ends of said fingers and is below said palm region, and said thumb ball region extends across the entire width from said base of said thumb portion to said edge below said fifth finger portion.

2. The glove according to claim 1, wherein said finger portions are independently curved along a common arc.

3. The glove according to claim 2, wherein said glove is formed to resemble a relaxed human hand.

4. The glove according to claim 1, wherein a bottom portion of the glove comprises a cuff portion having a diameter selected so that the cuff portion grips the wearer's wrist or forearm.

5. The glove according to claim 1, wherein said glove is comprised of an elastomeric material.

6. The glove according to claim 5, wherein said elastomeric material comprises, natural rubber, silicone rubber or nitrile rubber.

7. The glove according to claim 1, wherein said thumb ball area merges with and is integral with a region immediately below the fifth finger that is configured to accommodate a fleshy portion of the wearer's hand below the fifth finger.

8. An anatomically-accurate elastomeric surgical glove, comprising:

a palm region;

a plurality of finger portions which extend from base ends of said finger portions upward from said palm region;

a thumb portion at one side of a width of said glove; and an enlarged thumb ball area which extends across said width of said glove below said palm region from a base of the thumb portion to a side of the glove opposite the thumb portion at an edge of the glove below a fifth finger portion and which increases the circumference of the glove across a lower portion of said glove below said palm region to reduce the amount that the glove stretches when a wearer's hand moves into certain positions;

said thumb ball region is substantially below said base ends of said fingers and is below said palm region, and said thumb ball region extends across the entire said width from said base of said thumb portion to said edge below said fifth finger portion;

said finger portions are independently curved along a common arc;

said glove is comprised of an elastomeric material; and said thumb ball area merges with and is integral with a region immediately below the fifth finger that is configured to accommodate a fleshy portion of the wearer's hand below the fifth finger.

* * * * *